United States Patent
Wang et al.

(10) Patent No.: US 12,097,113 B2
(45) Date of Patent: Sep. 24, 2024

(54) BIOPROSTHETIC VALVE AND PREPARATION METHOD THEREOF

(71) Applicant: Sichuan University, Chengdu (CN)

(72) Inventors: Yunbing Wang, Chengdu (CN); Gaoyang Guo, Chengdu (CN); Li Yang, Chengdu (CN)

(73) Assignee: Sichuan University, Chengdu (CN)

( * ) Notice: Subject to any disclaimer, the term of this patent is extended or adjusted under 35 U.S.C. 154(b) by 797 days.

(21) Appl. No.: 17/115,812

(22) Filed: Dec. 9, 2020

(65) Prior Publication Data
US 2021/0338420 A1 Nov. 4, 2021

Related U.S. Application Data

(63) Continuation of application No. PCT/CN2020/123352, filed on Oct. 23, 2020.

(30) Foreign Application Priority Data
Apr. 24, 2020 (CN) .......................... 202010331262.1

(51) Int. Cl.
*A61F 2/24* (2006.01)
*A61L 27/36* (2006.01)
(Continued)

(52) U.S. Cl.
CPC .......... *A61F 2/2415* (2013.01); *A61F 2/2418* (2013.01); *A61L 27/3625* (2013.01);
(Continued)

(58) Field of Classification Search
CPC ............. A61L 27/3625; A61L 2430/20; A61L 33/0011; A61L 33/0041; A61L 33/0088; A61F 2/2415
See application file for complete search history.

(56) References Cited

U.S. PATENT DOCUMENTS 6,702,851 B1  3/2004  Chinn et al.
9,272,075 B2  3/2016  Antoni et al.

FOREIGN PATENT DOCUMENTS

CN  105682609 A  6/2016
CN  106730051 A  5/2017
(Continued)

OTHER PUBLICATIONS

Wei-Hsuan Kuo, et al., Surface Modification with Poly(sulfobetaine methacrylate-co-acrylic acid) To Reduce Fibrinogen Adsorption, Platelet Adhesion, and Plasma Coagulation, Biomacromolecules, 2011, pp. 4348-4356, vol. 12.

*Primary Examiner* — Javier G Blanco
(74) *Attorney, Agent, or Firm* — Bayramoglu Law Offices LLC (57) ABSTRACT

A bioprosthetic valve and a preparation method thereof are provided. The bioprosthetic valve includes a stent and a functional biological tissue material attached to the stent. The functional biological tissue material is a biologicaltissue covalently bonded with an active group and a functional molecule or group. The method improves the anti-thrombosis and anti-calcification functions by covalently modifying the surface of a biological valve using an active group and a functional molecule or group with a substantial degree of grafting. The new bioprosthetic valve does not include aldehyde residues, exhibits excellent biocompatibility, optimal mechanical properties, high stability, and can meet the performance requirements of a biological valve delivered through a catheter.

8 Claims, 8 Drawing Sheets

(51) Int. Cl.
*A61L 27/54* (2006.01)
*A61L 31/00* (2006.01)
*A61L 33/00* (2006.01)
*A61L 33/04* (2006.01)

(52) U.S. Cl.
CPC ........... *A61L 27/3687* (2013.01); *A61L 27/54* (2013.01); *A61L 31/005* (2013.01); *A61L 33/0023* (2013.01); *A61L 33/0041* (2013.01); *A61L 33/04* (2013.01); *A61L 2300/208* (2013.01); *A61L 2430/20* (2013.01)

(56) References Cited

FOREIGN PATENT DOCUMENTS

| | | | | |
|---|---|---|---|---|
| CN | 109481085 A | | 3/2019 | |
| CN | 109833519 A | * | 6/2019 | |
| CN | 110101911 A | * | 8/2019 | ............. A61L 27/16 |
| CN | 111494717 A | | 8/2020 | |
| JP | S6253666 A | | 3/1987 | |
| WO | WO-2006026325 A2 | * | 3/2006 | ............. A61K 35/12 |
| WO | WO-2016172460 A1 | * | 10/2016 | ............. A61L 27/34 |

* cited by examiner

BIOPROSTHETIC VALVE AND PREPARATION METHOD THEREOF

CROSS REFERENCE TO THE RELATED APPLICATIONS

This application is a continuation application of the International Application PCT/CN2020/123352, filed on Oct. 23, 2020, which is based upon and claims priority to Chinese Patent Application No. 202010331262.1, filed on Apr. 24, 2020, the entire contents of which are incorporated herein by reference.

TECHNICAL FIELD

The present invention relates to the technical field of medical materials, and more particularly, to a bioprosthetic valve and a preparation method thereof.

BACKGROUND

Valves keep blood moving through the heart in the right direction and are important organs of the human body. Valvular diseases seriously affect the quality of life and safety of patients. Human valves are divided into two main categories: heart valves located at the heart and venous valves distributed in veins throughout the body. The heart valves control one-way flow of blood by opening and closing sequentially. Once diseased or damaged, the heart valves will hinder normal blood circulation, which will in turn increase strain on the heart and even lead to heart failure. The venous valves ensure unidirectional blood flow in veins toward the opening and closing in one direction, like a check valve. If venous valves function abnormally, problems and conditions can result, including venous blood reflux and venous hypertension, tortuous expansion of superficial veins, tissue edema, skin lipid sclerosis, local pigmentation and venous ulceration.

For most patients with valvular diseases, conventional treatment methods temporarily control the condition, but cannot fundamentally solve the problem of valvular function loss. This presents a high risk of recurrence and deterioration. Therefore, valve replacement surgery is ultimately required, that is, the original diseased valve is replaced with a bioprosthetic valve to maintain normal blood flow in the body.

A bioprosthetic valve can be installed on a delivery system and delivered transcutaneously to a valve lesion through a catheter to replace the bioprosthetic valve. The transcatheter bioprosthetic valve replacement method conforms to the concept and technology of minimally invasive therapy (MIT), which greatly reduces the risk and difficulty of the surgery and shortens postoperative convalescence.

In recent years, clinical trials have proven the effectiveness and safety of transcatheter bioprosthetic heart valves. Implanted bioprosthetic heart valves typically have a shorter lifespan than the native valve, and the problems of valve leaflet thrombosis and valve leaflet calcification often occur after implantation. Clinical data show that valve leaflet thrombosis can occur during the implantation process and may have an occurrence rate of 15%-40%. The leaflet and stent of a bioprosthetic heart valve have internal sinus areas, and in vitro hydrodynamic simulation experiments have shown that these internal sinus areas have a significantly lower blood flow velocity than that of the central area of the valve. This is likely to cause blockage of blood flow thus prolonging the contact time between blood and the valve leaflet. As a major component of a bioprosthetic valve that contacts blood, the valve leaflet is an important component for thrombosis.

The valve leaflets are usually prepared from xenobiological tissues with a large amount of collagen. Collagen promotes adhesion and activation of platelets and the local enrichment of coagulation factors, thereby causing valve leaflet thrombosis. Calcification in bioprosthetic heart valves generally occurs ten years after implantation. The calcification causes the valve leaflets to become hard and brittle, so the valve leaflets will have difficulty in opening and closing or even fail. A patient may require a second valve implantation operation as a result.

The leaflet materials in transcatheter bioprosthetic valves currently used in clinical practice are derived from glutaraldehyde-fixed xenogeneic tissues. Common glutaraldehyde cross-linking methods utilized promote calcification due to residual aldehyde groups, unstable cross-linking and inflammation. Technologies made and sold by Edwards Lifesciences Corporation under the trademark THERMAFIX technology and a proprietary alpha amino oleic acid process provided by Medtronic under the trademark AOA technology exhibit some efficacy for the calcification problem of glutaraldehyde-crosslinked in bioprosthetic valves, but these technologies cannot completely avoid the problems caused by glutaraldehyde cross-linking and resulting free aldehyde groups, unstable cross-linking and poor biocompatibility. Additionally, these technologies cannot alleviate the thrombosis problem. Other compounds such as epoxy compounds, 1-(3-dimethylaminopropyl)-3-ethylcarbodiimide hydrochloride (EDC) and genipin are used to cross-link bioprosthetic valves, which can improve biocompatibility and reduce calcification, but still cannot solve the thrombosis problem. Therefore, prior technologies cannot simultaneously solve the thrombosis and calcification problems to which transcatheter bioprosthetic valves are susceptible.

The concept of transcatheter deep vein replacement was first proposed by professor Dotter in the United States in 1981. Subsequently, many research centers used valves and stents of different materials and structures to study the technology. Uflacker et al. constructed a single-leaflet venous valve using a polyether polyurethane film, which was transcutaneously released into the inferior vena cava (IVC) of an experimental pig; Gomez Jorge et al. constructed a venous valve using a bovine jugular vein tanned with glutaraldehyde, which was transcutaneously released into the IVC or iliac vein of an experimental pig; and Pavcnik et al. constructed a valve using non-immunogenic pig small intestinal submucosa (SIS), which was released to the jugular vein of sheep through a catheter, and clinical trials were conducted.

Although these methods have proven efficacious, there are still no products that can be clinically applied on a large scale. The most troublesome problem is subsequent occurrence or reoccurrence of thrombosis at the transplanted valve site following implantation. With a relatively-low flow velocity, blood in veins stays on a valve leaflet material for a long time. In addition, when a valve leaflet is closed, local blood flow blockage tends to form upstream of the normal blood flow between the valve leaflet and the stent, which will also extend the contact time between the blood and the local leaflet material, resulting in an increased risk of thrombosis.

Therefore, thrombosis is an equally serious and non-negligible risk for both heart and venous valves. The valve leaflet material, as an important catalyst of thrombosis, is one of the problems that needs urgent resolution. In order to solve the thrombosis problem heretofore caused by a xenograft, the surface of the xenograft is often modified with anticoagulant molecules by the covalent method. This method can maintain the anticoagulant property for a suspended period, however, covalent modification commonly causes a reduction of anticoagulant activity, heavily depends on modification sites and modification density, and often results in an undesired anticoagulant effect on the modified surface.

SUMMARY

In view of the above-mentioned problems in the prior art, the present invention provides a bioprosthetic heart valve and a preparation method thereof. The method improves the anti-thrombosis and anti-calcification functions by covalently modifying the surface of a biological valve using an active group and a functional molecule or group with substantial grafting capability. The prepared bioprosthetic valve does not include aldehyde residues, exhibits excellent biocompatibility, has optimal mechanical properties, is highly stability, and can meet the service performance requirements of the bioprosthetic valve delivered through a catheter.

To achieve the above objective, the present invention adopts the following technical solutions to solve the technical problems.

The present invention provides a bioprosthetic valve, including a stent and a functional biological tissue material attached to the stent. The functional biological tissue material is a biological tissue linked with an active group and a functional molecule or group. The active group and the functional molecule or group are all linked to the biological tissue by covalent bonds.

The functional molecule or group is at least one of heparin (15,000 Mw), hyaluronic acid (HA), polyethylene glycol (PEG), argatroban, low-molecular-weight heparin (LMWH; 4,500 Mw-5,000 Mw), hirudin, bivalirudin, fucoidan, peptide ACH11, antithrombin-III, sodium citrate, albumin, urokinase, hydroxyl, sulfonyl, sulfophenyl and zwitterion.

Further, a structural formula of the zwitterion is shown as follows:

and
the above structural formulas are named in sequence as follows:
N,N-dimethyl-N-methacrylamidopropyl-methanesulfonic acid zwitterion;
N,N-dimethyl-N-acrylamidopropyl-methanesulfonic acid zwitterion;
N,N-dimethyl-N-methacrylamidopropyl-methanecarboxylic acid zwitterion;
N,N-dimethyl-N-methacrylamidopropyl-methanecarboxylic acid zwitterion;
[2-(methacryloyloxy)ethyl]dimethyl-(3-sulfopropyl) ammonium hydroxide (SBMA);
[2-(acryloyloxy)ethyl]dimethyl-(3-sulfopropyl) ammonium hydroxide;
3-[[2-(methacryloyloxy)ethyl]dimethylammonio]propionate (CBMA);
3-[[2-(acryloyloxy)ethyl]dimethylammonio]propionate; and
2-methacryloyloxyethyl phosphocholine (MPC).
Preferably, the zwitterion is SBMA, CBMA, or MPC.
The bioprosthetic valve is a heart valve or a venous valve.
Further, the functional biological tissue material is prepared by soaking a biological tissue in deionized water, and adding the active group to enable a volume concentration of the active groups is 3-10%; after reacting at room temperature for 12-36 h, washing the biological tissue; soaking the washed biological tissue in a functional molecule or group solution overnight at 35° C.-40° C., where, a final concentration of the functional molecule or group is 20 mM-500 mM; and adding an initiator for initiating polymerization.
Further, the active group is added to enable the volume concentration of the active groups is 4%, followed by reacting at room temperature for 24 h.

Further, the washed biological tissue is soaked in the functional molecule or group solution overnight at 37° C., where, the final concentration of the functional molecule or group is 500 mM.

Further, the biological tissue is pericardium, aortic root, aortic valve, pulmonary root, pulmonary valve, tendon, ligament, skin, dura, peritoneum, blood vessel, pleura, diaphragm, mitral valve, or tricuspid valve.

Further, the active group is acrylamide, methacrylamide, acrylate, methacrylate or allyl group.

Further, the active group is linked to the biological tissue via an amide bond, and the functional molecule or group is also linked to the biological tissue via an amide bond, and more than two linking sites are arranged between the functional molecule or group and the biological tissue.

Further, a weight of the functional molecule or group is 1-30% of a dry weight of the functional biological tissue material; and preferably, the weight of the functional molecule or group is 24.6% of the dry weight of the functional biological tissue material.

Further, the polymerization initiated by the initiator is conducted at a temperature of no more than 50° C., and preferably at 37° C.

Further, the initiator is a thermal initiator or a photoinitiator. The thermal initiator is an organic peroxide initiator, an inorganic peroxide initiator, an azo initiator, or a redox initiator, and preferably a redox initiator, such as an ammonium persulfate (APS)/sodium bisulfite system. The photoinitiator is Irgacure D-2959.

Further, the stent includes, but is not limited to, a nickel-titanium alloy stent or a cobalt-chromium alloy stent.

A preparation method of the bioprosthetic valve, including the following steps:

preparing a functional biological tissue material, cutting the functional biological tissue material to form a tissue valve leaflet assembly, and attaching the assembly to a stent to obtain the bioprosthetic valve.

Further, after the tissue valve leaflet assembly is attached to the stent, it is sterilized, then packaged, and stored in a sterile solution, such as an ethanol aqueous solution, a peracetic acid (PAA) aqueous solution or a glutaraldehyde aqueous solution.

The bioprosthetic valve and the preparation method thereof provided in the present invention have the following advantages:

The bioprosthetic valve provided by the present invention has prominent anti-coagulation and anti-calcification functions, and the implanted valve leaflet undergoes a lower incidence of thrombosis and calcification than the prior interventional bioprosthetic valves. The leaflets of the interventional bioprosthetic valve of the present invention are made from a biological tissue (a functional biological tissue material) with anti-coagulation and anti-calcification functions. The biological tissue is subjected to a special cross-linking treatment, then cut into a specific geometric shape, and attached to a stent to obtain an implantable bioprosthetic valve. The implantable bioprosthetic valve is installed on a catheter delivery system before the operation, by which the bioprosthetic valve can be delivered to a designated location through a blood vessel to achieve the valve replacement. The bioprosthetic valve provided by the present invention can be a heart valve and a venous valve, which can be used for valve replacement by minimally invasive intervention to reduce the operation risk.

The biological tissue with anti-coagulation and anti-calcification functions (a functional biological tissue material) in the present invention is a crosslinked biological tissue with anti-coagulation and anti-calcification functions obtained by introducing an active group that can undergo polymerization into a biological tissue and copolymerizing the tissue with the active group and a functional monomer radical. The introduction of the functional molecule through a cross-linking can improve the anti-thrombosis and anti-calcification functions of the bioprosthetic valve. The introduction of the functional molecule with a substantial grafting capability can reduce the adhesion of plasma proteins and platelets to prevent thrombosis and further reduce calcification caused by thrombosis, and can also promote the in situ endothelialization of the bioprosthetic valve to form a blood compatibility barrier, thereby preventing calcium deposition. Moreover, the multi-site cross-linking among collagens realizes the full cross-linking in and among collagen fibers, so it can provide better flexibility and the function of dispersing stress to improve the fatigue performance and in-vivo stability of the bioprosthetic valve.

DETAILED DESCRIPTION OF THE EMBODIMENTS

Embodiment 1 Preparation of a Functional Biological Tissue Material (a Biological Material with Anti-Coagulation and Anti-Calcification)

Figure 2:
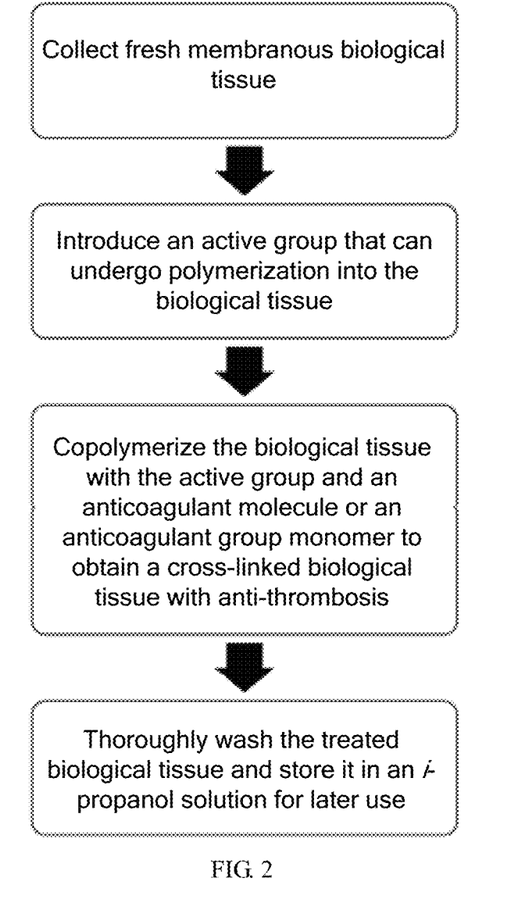
FIG. 2 is a flow chart of the preparation of a biological tissue with anti-thrombosis and anti-calcification.
Figure 3:
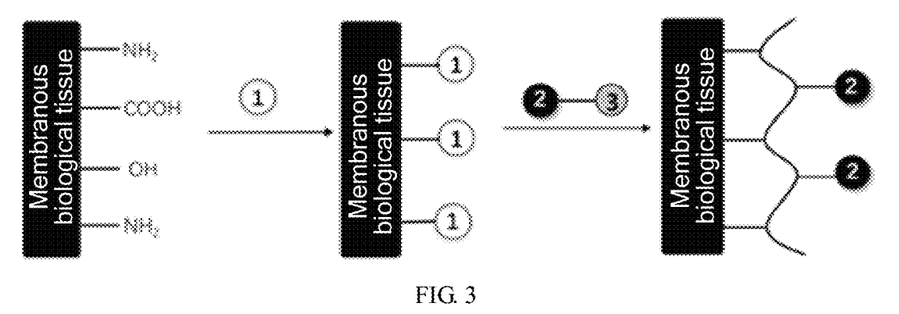
FIG. 3 is a schematic diagram illustrating the preparation mechanism of the functional biological tissue with anti-thrombosis and anti-calcification, where, the characters (1)-3 represent different functional molecules or groups.
Figure 4:
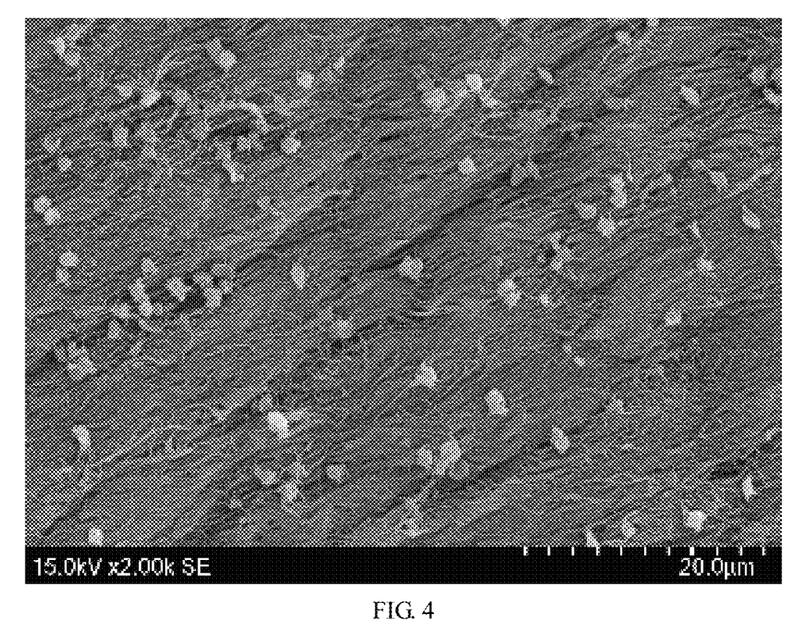
FIG. 4 is a scanning electron microscope (SEM) image illustrating the platelet adsorption of an MPC-20 biological tissue.
Figure 5:
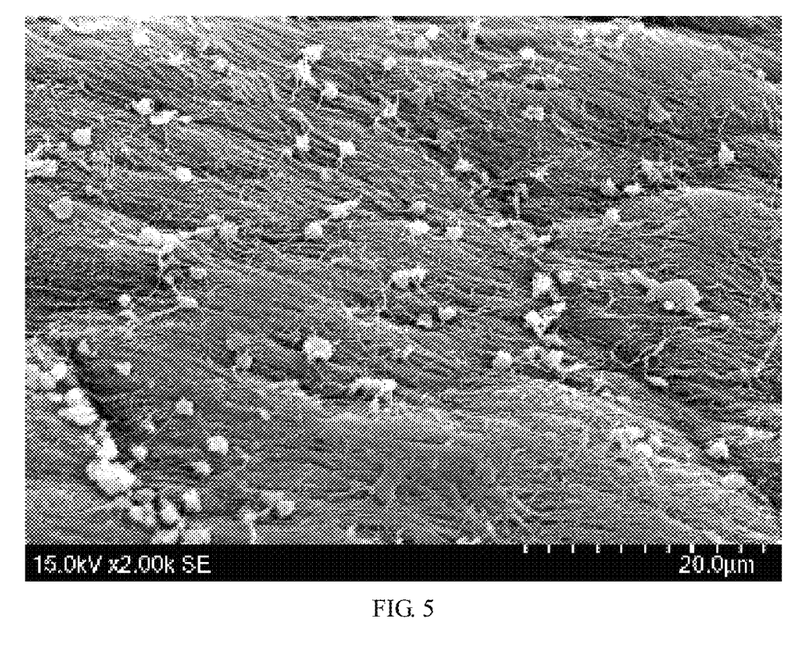
FIG. 5 is an SEM image illustrating the platelet adsorption of an MPC-500 biological tissue.
Figure 6:
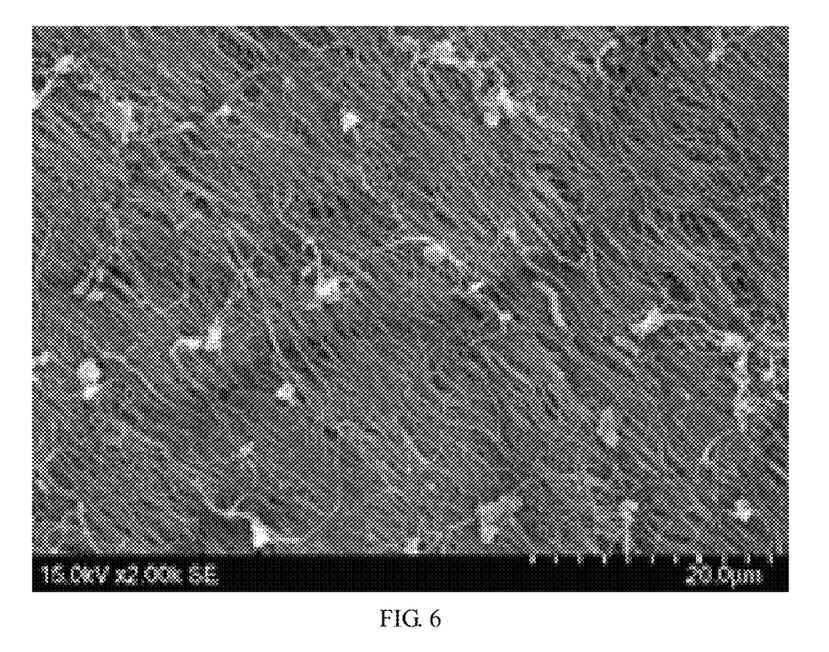
FIG. 6 is an SEM image illustrating the platelet adsorption of an SBMA-20 biological tissue.
Figure 7:
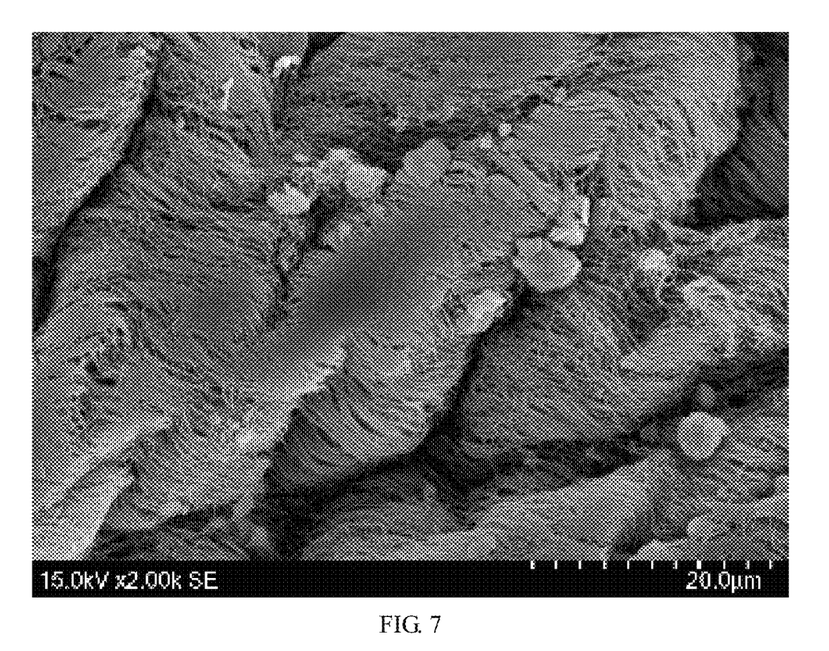
FIG. 7 is an SEM image illustrating the platelet adsorption of an SBMA-500 biological tissue.
Figure 8:
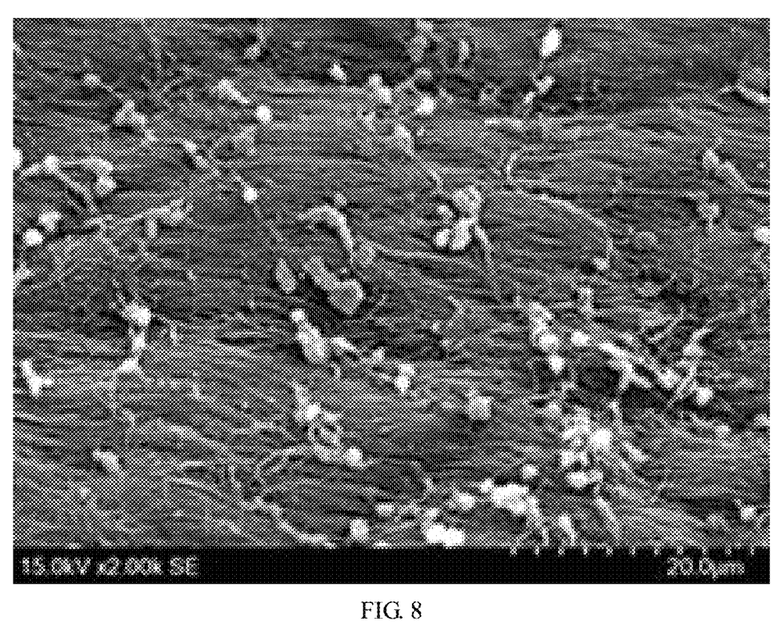
FIG. 8 is an SEM image illustrating the platelet adsorption of an unmodified biological tissue.
Figure 9:
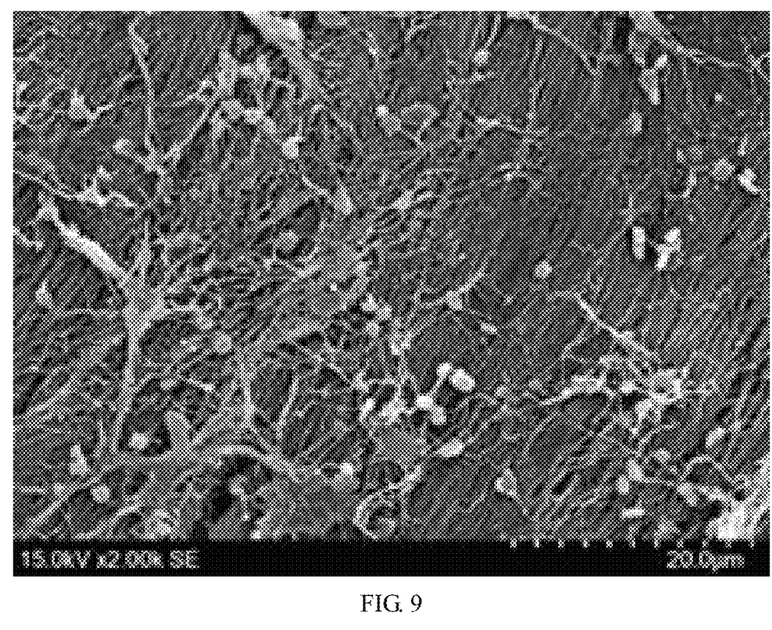
FIG. 9 is an SEM image illustrating the platelet adsorption of a glutaraldehyde-crosslinked biological tissue.

The preparation flow chart is shown in FIG. 2, and the preparation mechanism is shown in FIG. 3. The specific steps were as follows:

Fresh porcine pericardium was thoroughly washed with deionized water and then immersed in deionized water; methacrylic anhydride was added dropwise in a 4° C. ice bath under stirring to enable a final concentration of the anhydride is 4% (v/v), and the pH was adjusted to 7 with a sodium hydroxide solution; after the dropwise addition was completed, reaction was conducted at room temperature for 24 h; the porcine pericardium modified with methacrylic anhydride was thoroughly washed and then soaked overnight at 37° C. in a zwitterionic monomer solution with a final concentration shown in the table below; then an initiator was added for cross-linking, and reaction was conducted at 37° C. for 24 h to obtain the functional biological tissue material. The obtained porcine pericardium was thoroughly washed with deionized water and then stored in a 25% isopropanol (i-propanol) solution for later use.

Unmodified biological tissue: the preparation steps before the initiator was added for cross-linking were the same as above, but the porcine pericardium was directly added with the initiator for cross-linking without being soaked in the monomer solution. The obtained porcine pericardium was thoroughly washed with deionized water and then stored in a 25% i-propanol solution for later use.

The specific parameters are as follows:

| Sample name | Type and concentration of monomer | Initiator concentration | MPC/SBMA content (w/w) |
| --- | --- | --- | --- |
| MPC-20 | MPC: 20 mM | 50 mM APS and 50 mM sodium bisulfite | 1.6% |
| MPC-500 | MPC: 500 mM | 50 mM APS and 50 mM sodium bisulfite | 15.6% |
| SBMA-20 | SBMA: 20 mM | 50 mM APS and 50 mM sodium bisulfite | 5.2% |
| SBMA-500 | SBMA: 500 mM | 50 mM APS and 50 mM sodium bisulfite | 24.6% |
| Unmodified | 0 | 50 mM APS and 50 mM sodium bisulfite | 0%* |

Notes:
SBMA: [2-(methacryloyloxy)ethyl]dimethyl-(3-sulfopropyl)ammonium hydroxide; MPC: 2-methacryloyloxyethyl phosphocholine;
*Unmodified is used as a baseline, set as 0%; Initiator concentration refers to the concentration of an initiator immediately after being added to a reaction system; and MPC/SBMA content refers to the content of MPC/SBMA in a prepared biological material that is lyophilized.

Since the functional molecule MPC includes phosphorus which is almost not found in biological materials, and SBMA includes unique sulfur, inductively coupled plasma-optic emission spectroscopy (ICP-OES) can be used to analyze the content of sulfur or phosphorus in a biological material, which can be converted into the content of a functional molecule, so as to obtain the modification degree of the functional molecule on the biological tissue, facilitating the screening of experimental conditions.

The specific conversion method is as follows:

$$\text{Functional molecule content (\%)} = \frac{C_{S(P)} \times 10 / M_{S(P)} \times M_{SBMA(MPC)}}{W} \times 100\%$$

where, $C_{S(P)}$ (mg/L) is a concentration of sulfur or phosphorus in a solution determined by ICP-OES; $M_{S(P)}$ is a relative atomic mass of sulfur or phosphorus; $M_{SBMA(MPC)}$ is a relative molecular mass of a functional molecule; and W (mg) is a dry weight of a biological material.

It can be seen from the above table that, compared with the control group, the biological material prepared in the present invention shows that the biological tissue is well modified with the functional molecule, especially the SBMA-500 group, with the highest modification degree.

Embodiment 2 Anticoagulant Performance of the Biological Material with Anti-Coagulation and Anti-Calcification The prepared biological material with anti-coagulation and anti-calcification was washed, cut into a suitable size, and incubated with platelet-rich plasma (PRP) for 1 h. The amount of lactate dehydrogenase (LDH) after platelets lysis adhered to the material was determined to indicate the number of adhered platelets, and the results are shown in the table below. The adhesion of platelets on the material was observed by SEM, and the specific results are shown in FIG. 4-FIG. 9.

| Sample name | Absorbance value (490 nm) |
| --- | --- |
| MPC-20 | 0.30 |
| MPC-500 | 0.29 |
| SBMA-20 | 0.24 |
| SBMA-500 | 0.110 |
| Unmodified | 0.32 |
| Glutaraldehyde-crosslinked | 0.35 |

It can be seen from the above table that the higher the absorbance value at 490 nm, the higher the content of LDH, that is, the more the platelets adhered to the material. Therefore, it can be seen from the above table that the biological material prepared in the present invention exhibits an anticoagulant effect significantly better than the anticoagulant effect of the unmodified biological tissue and the glutaraldehyde-crosslinked biological tissue (porcine pericardium was subjected to cross-linking for 24 h at room temperature and pH=7.4 in a glutaraldehyde aqueous solution with a volume concentration of 0.625%, and obtained porcine pericardium was dehydrated and dried). The SBMA-modified biological tissue exhibits a better anticoagulant effect than the MPC-modified biological tissue, and the SBMA-modified biological tissue with substantial grafting capability exhibits the best anticoagulant effect.

It can be seen from FIG. 4-FIG. 9 that the biological material prepared in the present invention exhibits an anticoagulant effect significantly better than the anticoagulant effect of the unmodified biological tissue and the glutaraldehyde-crosslinked biological tissue (porcine pericardium was subjected to cross-linking for 24 h at room temperature and pH=7.4 in a glutaraldehyde aqueous solution with a volume concentration of 0.625%, and obtained porcine pericardium was dehydrated and dried). The SBMA-modified biological tissue exhibits a better anticoagulant effect than the MPC-modified biological tissue, and the SBMA-modified biological tissue with substantial grafting capability exhibits the best anticoagulant effect.

The qualitative observation results of SEM in FIG. 4-FIG. 9 are consistent with the quantitative measurement results of LDH.

Embodiment 3 Endothelialization Performance of the Biological Material with Anti-Coagulation and Anti-Calcification The prepared biological material with anti-coagulation and anti-calcification was inoculated with endothelial cells on the surface, then incubated for 3 days, and stained with DAPI- and FITC-labeled phalloidin. The results are shown in FIG. 10-FIG. 12.

Figure 10:
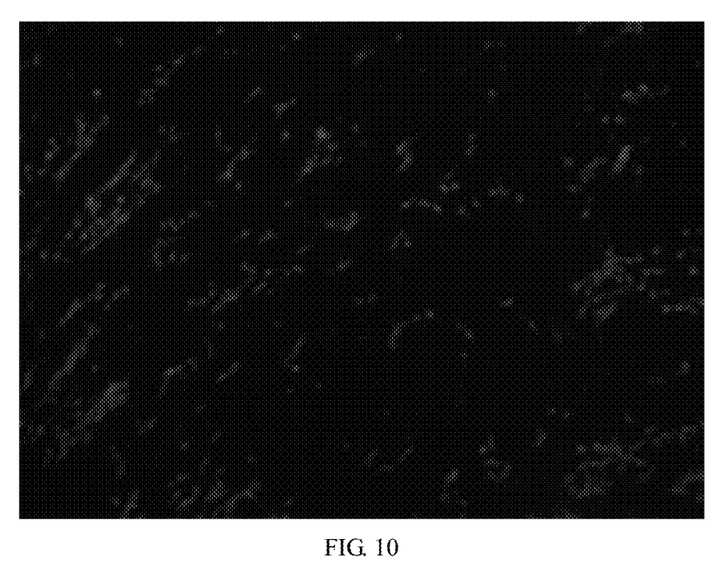
FIG. 10 is a diagram illustrating the growth of endothelial cells on the SBMA-500 biological tissue under a fluorescence microscope.
Figure 11:
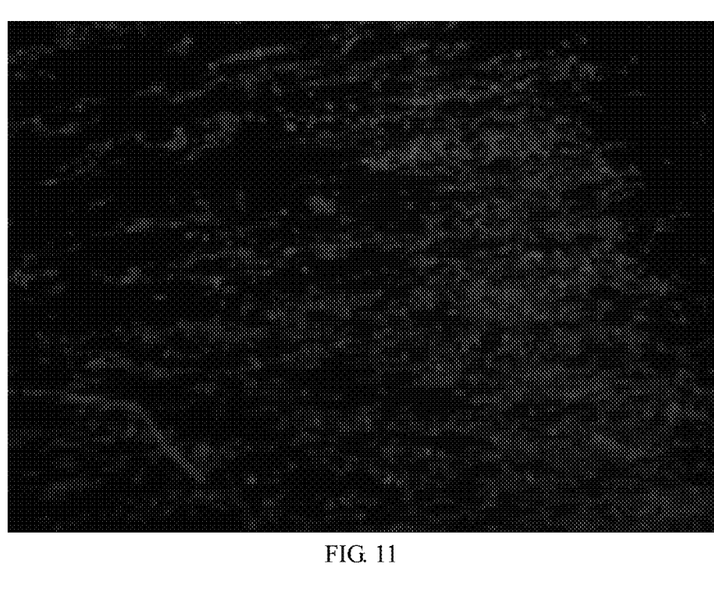
FIG. 11 is a diagram illustrating the growth of endothelial cells on the unmodified biological tissue under the fluorescence microscope.
Figure 12:
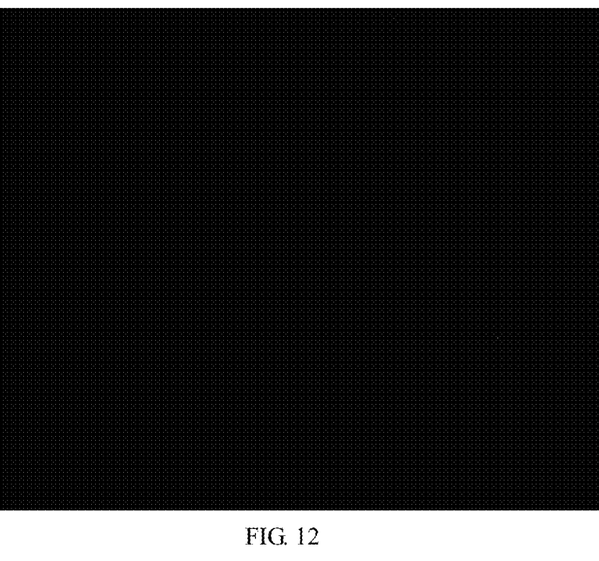
FIG. 12 is a diagram illustrating the growth of endothelial cells on the glutaraldehyde-crosslinked biological tissue under the fluorescence microscope.

It can be seen from FIG. 10-FIG. 12 that the growth of endothelial cells on the SBMA-500 modified biological tissue is better than the growth of endothelial cells on the unmodified and glutaraldehyde-crosslinked biological tissues.

Embodiment 4 Characterization of Anti-Calcification and Immune Response of the Biological Material with Anti-Coagulation and Anti-Calcification The prepared biological material with anti-coagulation and anti-calcification was cut into 1 cm² sheets, implanted subcutaneously into Sprague-Dawley (SD) rats, and taken out 90 days later. The calcium content in the sample was determined by ICP-OES. The results are as follows:

| Sample name | Calcium content (g/kg) |
|---|---|
| SBMA-500 | 12.8 |
| Unmodified | 38.4 |
| Glutaraldehyde-crosslinked | 117.3 |

It can be seen from the above table that the calcification degree of the SBMA-500 modified biological tissue is significantly lower than the calcification degree of the unmodified and glutaraldehyde-crosslinked biological tissues.

Embodiment 5 Stability of the Biological Material with Anti-Coagulation and Anti-Calcification The prepared biological material with anti-coagulation and anti-calcification was cut into small pieces of 3-8 mg, and the moisture on the surface was removed with filter paper. The sample was put in an aluminum crucible and sealed, and the crucible with the sample was placed in an instrument for conducting thermal denaturation temperature analysis by differential scanning calorimeter (DSC), to characterize the stability of the biological tissue. The results are as follows:

| Sample name | Thermal denaturation temperature (° C.) |
|---|---|
| SBMA-500 | 80.15 |
| Fresh tissue | 68.88 |

It can be seen from the above table that the biological material with anti-coagulation and anti-calcification prepared in the present invention exhibits stronger high-temperature-resistance than fresh tissue, indicating that the biological tissue has superior stability.

Embodiment 6 Implantation of a Vascular Graft of the Biological Material with Anti-Coagulation and Anti-Calcification The prepared biological material with anti-coagulation and anti-calcification was rolled into a tube with a diameter of about 2 mm, and a medical adhesive was used at the interface for bonding. The moisture on the surface was removed with filter paper. Then the tube was weighed, and recorded. The vascular anastomosis was used to replace a rabbit carotid artery with a length of about 2 cm. A period of time after the implantation, the material was taken out for observation. The moisture on the surface of the material was removed with filter paper, then the material was weighed again, and the weight gain was calculated, namely, the thrombus production. The results are as follows:

| Sample name | Initial weight (mg) | Final weight (mg) | Thrombus production (mg) |
|---|---|---|---|
| SBMA-500 | 80.9 | 83.6 | 2.7 |
| Unmodified | 78.6 | 262.4 | 183.8 |
| Glutaraldehyde-crosslinked | 82.5 | 295.3 | 212.8 |

It can be seen from the above table that there is a thrombus production more than 2 times the tissue weight in the glutaraldehyde-crosslinked and unmodified biological tissues, and there is almost no thrombus production in the SBMA-500.

Figure 1:
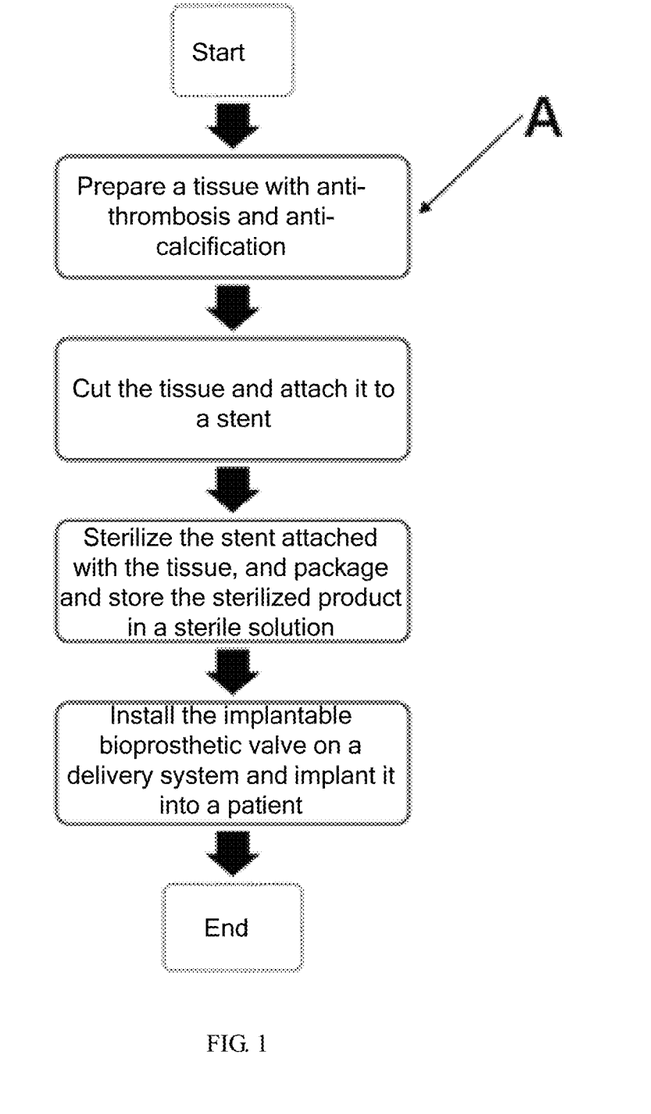
FIG. 1 is a flow chart of the preparation of a bioprosthetic valve.

Embodiment 7 Preparation of a Bioprosthetic Valve (See FIG. 1 for the Preparation Process)

The biological tissue material with anti-coagulation and anti-calcification prepared in embodiment 1 that had an SBMA monomer concentration of 500 mM was laser-cut to form a tissue valve leaflet assembly, and the tissue valve leaflet assembly was attached to a nickel-titanium alloy stent by suturing to obtain an implantable bioprosthetic valve.

Figure 13:
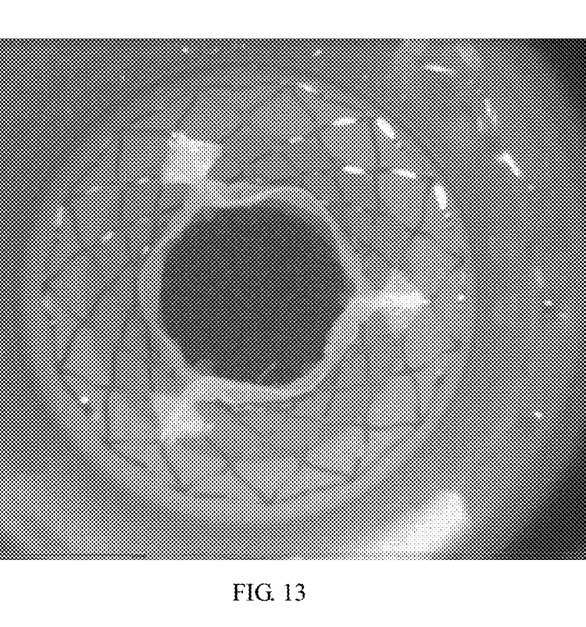
FIG. 13 is a diagram illustrating the pulsatile flow of a bioprosthetic valve made from the SBMA-500 (open state).
Figure 14:
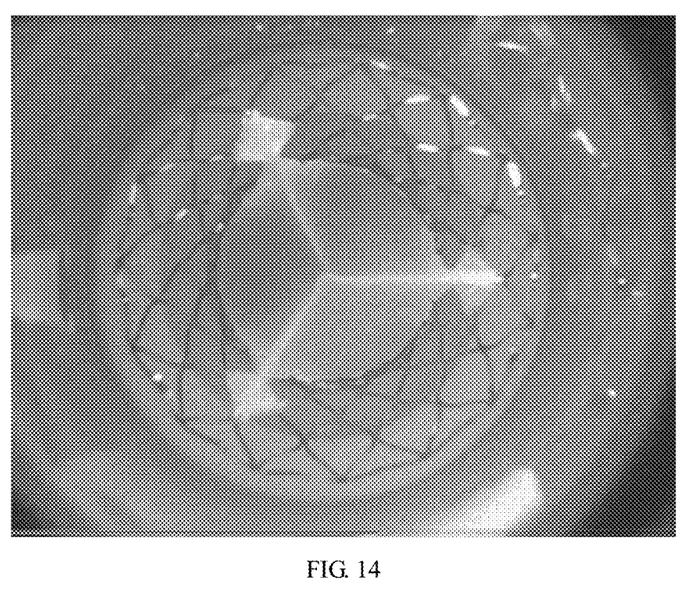
FIG. 14 is a diagram illustrating the pulsatile flow of a bioprosthetic valve made from the SBMA-500 (closed state).

Embodiment 8 In Vitro Hydrodynamic Performance Test of the Bioprosthetic Heart Valve A optimal bioprosthetic heart valve with a diameter of 29 mm (modified with SBMA-500) was subjected to an in vitro hydrodynamic performance test under standard test conditions (heart rate: 70 beats/min, average cardiac output: 5 L/min, and average aortic pressure: 100 mmHg), and the following results were obtained: an effective opening area=2.855 cm² and regurgitation ratio=9.998%, which met the requirements in ISO 5840-1:2015, indicating that the bioprosthetic valve met the hydrodynamic requirements. The specific results are shown in FIG. 13 and FIG. 14.

Embodiment 9 In Vitro Accelerated Fatigue Performance Test of the Bioprosthetic Heart Valve The optimal bioprosthetic heart valve with a diameter of 29 mm (modified with SBMA-500) was subjected to an in vitro accelerated fatigue test on an in vitro accelerated fatigue tester. After 50 million heartbeats, the SBMA-500 modified valve still had excellent appearance, while leaflets of the unmodified biological valve were torn.

Embodiment 10 In Vivo Experiment on Implantation of a Bioprosthetic Venous Valve in Large Animals

A prepared bioprosthetic venous valve with a diameter of 12 mm (modified with SBMA-500) was sterilized and installed on a catheter delivery system before operation. The bioprosthetic valve was implanted into the iliac vein of a dog through the delivery system. The dog was followed up for 3 months, and then it was found through vascular ultrasound diagnosis that the vessel exhibited excellent patency, indicating that the SBMA-500 modified valve had a prominent anti-thrombosis function.

What is claimed is:

1. A bioprosthetic valve, comprising a stent and a functional biological tissue material, wherein the functional biological tissue material is attached to the stent, and the functional biological tissue material is a biological tissue linked with an active group and a zwitterion by covalent bonds;
wherein the active group is one selected from the group consisting of acrylamide, methacrylamide, acrylate, methacrylate, and allyl group;
wherein the zwitterion is selected from the group consisting of sulfobetaine methacrylate (SBMA), carboxybetaine methacrylate (CBMA), and 2-methacryloyloxyethyl phosphocholine (MPC);
wherein, the functional biological tissue material is prepared by:
soaking the biological tissue in deionized water to obtain a first mixture, and adding the active group into the first mixture to obtain a second mixture, wherein a volume concentration of the active group in the second mixture is 3%-10%;
performing a reaction on the second mixture at room temperature for 12-36 hours to obtain a reacted biological tissue;
washing the reacted biological tissue to obtain a washed biological tissue;
soaking the washed biological tissue in a zwitterionic monomer solution overnight at 35° C.-40° C., wherein, a final concentration of the zwitterion is 20 mM-500 mM; and
adding an initiator for initiating a polymerization.

2. The bioprosthetic valve according to claim 1, wherein, a structural formula of the zwitterion is shown as follows:

3. The bioprosthetic valve according to claim 1, wherein, the active group is added to enable the volume concentration of the active group to be 4%, followed by reacting at room temperature for 24 hours.

4. The bioprosthetic valve according to claim 1, wherein, the washed biological tissue is soaked in the zwitterionic monomer solution overnight at 37° C., wherein, the final concentration of the zwitterion is 500 mM.

5. The bioprosthetic valve according to claim 1, wherein, the biological tissue is one selected from the group consisting of pericardium, aortic root, aortic valve, pulmonary root, pulmonary valve, tendon, ligament, skin, dura, peritoneum, blood vessel, pleura, diaphragm, mitral valve and tricuspid valve.

6. The bioprosthetic valve according to claim 1, wherein, a weight of the zwitterion is 1%-30% of a dry weight of the functional biological tissue material.

7. The bioprosthetic valve according to claim 1, wherein, the polymerization initiated by the initiator is conducted at a temperature of no more than 50° C.

8. A preparation method of the bioprosthetic valve according to claim 1, comprising the following steps:
preparing the functional biological tissue material, cutting the functional biological tissue material to form a tissue valve leaflet assembly, and attaching the tissue valve leaflet assembly to the stent to obtain the bioprosthetic valve.

* * * * *